United States Patent [19]

Desai

[11] Patent Number: 5,455,255

[45] Date of Patent: Oct. 3, 1995

[54] 2-(2,3,5,6-TETRAFLUORO-4-PYRIDYL)-1,2-BENZISOTHIAZOL-3(2H)-ONE 1,1-DIOXIDES AND COMPOSITIONS AND METHOD OF USE THEREOF

[75] Inventor: Ranjit C. Desai, Towamencin Township, Pa.

[73] Assignee: Sterling Winthrop Inc., New York, N.Y.

[21] Appl. No.: 192,914

[22] Filed: Feb. 7, 1994

[51] Int. Cl.$^6$ .......................... C07D 417/04; A61K 31/44
[52] U.S. Cl. .......................... 514/338; 546/272; 544/131; 544/360; 514/236.8; 514/254
[58] Field of Search .............. 546/272; 514/338

[56] References Cited

U.S. PATENT DOCUMENTS

| | | | |
|---|---|---|---|
| 4,276,298 | 6/1981 | Jones et al. | 546/270 |
| 4,369,183 | 1/1983 | Jones et al. | 546/270 |

FOREIGN PATENT DOCUMENTS 26791  4/1981  European Pat. Off. .

OTHER PUBLICATIONS

Cha, Biochem. Pharmacol., 1975, 24, 2177–2185.
El–Maghraby et al., Proc. Indian Natl. Acad. Sci. Acad., Part A, 1987, 53(3), 431–440.
Yogi, et al., Bull. Chem. Soc. Jpn. 1987, 60, 731–735.
Badawi et al., Oriental J. Chem. 1986, 2(1), 40–44.
Rabhofer et al., Israel Journal of Chemistry 1979, 18, 249–252.
Rabhofer et al., Tetrahedron Lett. 1979, 14, 1217–1218.
Abramovitch et al., J. Org. Chem. 1974, 39(13), 1795–1801.
Ashe et al., J. Biol. Chem,. 1981, 256(22), 11603–11606.

*Primary Examiner*—Jane Fan
*Attorney, Agent, or Firm*—Michael D. Alexander; Paul E. Dupont

[57] ABSTRACT

2-(2,3,5,6-Tetrafluoro-4-pyridyl)-1,2-benzisothiazol-3(2H)one 1,1-dioxides of the formula I:

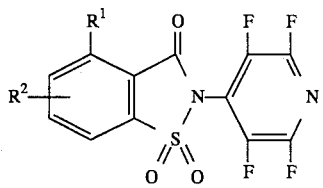

pharmaceutical compositions containing them and methods for the treatment of degenerative diseases utilizing them.

6 Claims, No Drawings

2-(2,3,5,6-TETRAFLUORO-4-PYRIDYL)-1, 2-BENZISOTHIAZOL-3(2H)-ONE 1,1-DIOXIDES AND COMPOSITIONS AND METHOD OF USE THEREOF

BACKGROUND OF THE INVENTION (a) Field of the Invention

The invention relates to 2-(2,3,5,6-tetrafluoro-4-pyridyl)-1,2-benzisothiazol-3(2H)-one 1,1-dioxides, to pharmaceutical compositions containing the same and to the method of use thereof in the treatment of degenerative disease.

(b) Information Disclosure Statement

The inhibition of proteolytic enzymes by nontoxic reagents is useful in the treatment of degenerative disorders, such as emphysema, rheumatoid arthritis and pancreatitis, in which proteolysis is a substantive element.

Protease inhibitors are widely utilized in biomedical research. Serine proteases are the most widely distributed class of proteolytic enzymes. Some serine proteases are characterized as chymotrypsin-like or elastase-like based upon their substrate specificity.

Chymotrypsin and chymotrypsin-like enzymes normally cleave peptide bonds in proteins at a site at which the amino acid residue on the carboxyl side is typically Trp, Tyr, Phe, Met, Leu or another amino acid residue which contains aromatic or large alkyl side chains.

Elastase and elastase-like enzymes normally cleave peptide bonds at a site at which the amino acid residue on the carboxyl side of the bond is typically Ala, Val, Set, Leu or other similar, smaller amino acids.

Both chymotrypsin-like and elastase-like enzymes are found in leukocytes, mast cells and pancreatic juice in higher organisms, and are secreted by many types of bacteria, yeast and parasites.

Cha, Blochem. Pharmacol., 1975, 24, 2177–2185, discusses kinetic approaches to the study of the binding of inhibitors to macromolecules, such as enzymes, and methods for the determination of such parameters as the inhibition constants, reaction rates and bound and unbound enzyme concentrations.

Jones et al. U.S. Pat. No. 4,369,183, issued Jan. 18, 1983 (a divisional of U.S. Pat. No. 4,276,298, issued Jun. 30, 1981, which in turn is a continuation-in-part of Ser. No. 889,762, filed Mar. 24, 1978, now abandoned) disclose compounds of the formula:

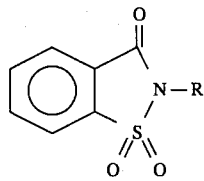

wherein R is

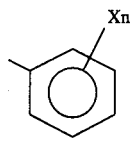

where n is 1 to 5; and X is independently selected from (1) fluoro; (2) nitro; except that where X is only nitro, n must be 2 and X must be 2,4- or 3,5-dinitro; (3) trifluoromethyl; (4) cyano; (5) $C_{1-3}$ alkoxycarbonyl; (6) $C_{1-3}$ alkylcarbonyl; (7) carboxy; (8) carbamoyl; (9) $C_{1-3}$ alkylacylamino; (10) $C_{1-3}$ alkylsulfonyl; (11) N,N-di-($C_{1-3}$ alkyl) sulfamyl; (12) trifluoromethoxy; (13) trifluoromethylthio; and (14) trifluoromethylsulfonyl; and (15) trifluoromethylsulfinyl or substituted pyridyl, where m has the same meaning as n above, and Y has the same meaning

as X, except that it may additionally be mono-nitro. The compounds are said to have protease enzyme inhibitory activity, especially elastase inhibitory activity, and to be useful in the treatment of emphysema, rheumatoid arthritis and various inflammatory diseases. Specifically disclosed are those compounds wherein R is 2,3,4,5,6-pentafluorophenyl, 3,5-dinitrophenyl, 3-nitropyrid- 2-yl, 3- or 5-nitropyrid-2-yl, 5-cyanopyrid-2-yl and 3,5-dinitropyrid-2-yl.

Jones et al. European Patent Application 26791, published Apr. 15, 1981, contains essentially the same disclosure as that shown in U.S. Pat. Nos. 4,369,183 and 4,276,298 which are described hereinabove.

El-Maghraby et al. Proc. Indian Natl. Sci. Acad., Part A, 1987, 53 (3), 431–440 disclose 6-nitro-2-(4-pyridinyl)-1,2-benzisothiazol- 3(2H)-one 1,1-dioxide and 6-nitro-2-(2-pyridinyl)- 1,2-benzisothiazol-3(2H)-one 1,1-dioxide. No utility is disclosed for these compounds.

Yogi et al. Bull. Chem. Soc. Jpn. 1987, 60, 731–735 disclose 2-(6-benzoyl-2-phenyl-3-pyridinyl)-2-benzisothiazol- 3(2H)-one 1,1-dioxide and 2-(6-chloro-2-phenyl-3-pyridinyl)-1,2-benzisothiazol- 3(2H)-one 1,1-dioxide without an indication of utility.

Badawi et al. Oriental J. Chem. 1986, 2(1), 40–44 disclose 6-(2-pyridinylsulfamoyl)-2-(2-pyridinyl)-1,2-benzisothiazol- 3-(2H)-one 1,1-dioxide as an amoebicidal agent.

Rabhofer et al. Israel Journal of Chemistry 1979, 18, 249–252 disclose 2-(2,3,5,6-tetrafluoro-4-pyridinyl)-1,2-benzisothiazol- 3(2H)-one 1,1-dioxide without an indication of utility. A similar disclosure can be found in Rabhofer et al., Tetrahedron Lett. 1979, 14, 1217–1218.

Abramovitch et al. J. Org. Chem 1974 39(13), 1795–1801 disclose 2-(2-pyridinyl)-1,2-benzisothiazol-3-(2H)-one 1,1-dioxide without an indication of utility.

Ashe et al. J. Biol. Chem. 1981, 256(22), 11603–11606 disclose a number of N-aryl-1,2-benziosothiazol-3(2H)-one 1,1-dioxides having inhibitory activity against human leukocyte and porcine pancreatic elastase.

SUMMARY OF THE INVENTION

The invention relates to compounds of the Formula I:

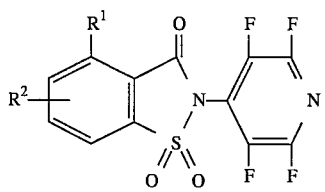

wherein:

$R^1$ is hydrogen, halogen, lower-alkyl, perfluorolower-alkyl, perchlorolower-alkyl, lower-alkenyl, lower-alkynyl, cyano, amino, lower-alkylamino, dilower-alkylamino, lower-alkoxy, benzyloxy, lower-alkoxycarbonyl or phenyl; and $R^2$ is hydrogen or from one to two, the same or different, substituents in any of the 5-, 6- or 7-positions selected from halogen, cyano, nitro, N=B, (where N=B is amino, lower-alkylamino, dilower-alkylamino, 1-azetidinyl, 1-pyrrolidinyl, 1-piperidinyl, 4-morpholinyl, 1-piperazinyl, 4-lower-alkyl-1-piperazinyl, 4-benzyl-1-piperazinyl, 1-imidazolyl, carboxy-lower-alkylamino, or —NR'—($C_1$–$C_{10}$-alkylene)—N(alkyl)$_2$, where R' is lower alkyl), 1-lower-alkyl-2-pyrrolyl, lower-alkylsulfonylamino, polyfluorolower-alkyl-sulfonylamino, polychlorolower-alkylsulfonylamino, aminosulfonyl, lower-alkyl, polyfluorolower-alkyl, polychlorolower-alkyl, cycloalkyl, lower-alkoxy, hydroxy, carboxy, carboxamido, hydroxy-lower-alkyl, methylenedioxy, cycloalkyloxy, formyl, aminomethyl, lower-alkylsulfonyl, polyfluorolower-alkylsulfonyl, polychlorolower-alkylsulfonyl, lower-alkylsulfonylaminosulfonyl, di(lower-alkyl)phosphonoxy, lower-alkoxypoly-lower-alkyleneoxy, hydroxy-lower-alkoxy, polyhydroxylower-alkoxy, or acetal or ketal thereof, poly(lower-alkoxy) lower-alkoxy, —SR, —SOR, —SO$_2$R, —OCOR, —O—($C_1$–$C_{10}$-alkylene)—COOR, —O—($C_1$–$C_{10}$-alkylene)-COOH, —O—($C_2$–$C_{10}$-alkylene)—N=B, where R is lower-alkyl, phenyl, benzyl or naphthyl, or phenyl or naphthyl substituted by from one to two substituents selected from lower-alkyl, lower-alkoxy or halogen and —N=B has the meanings given above;

or acid-addition salts of basic members thereof or base-addition salts of acidic members thereof, with the proviso that $R^1$ and $R^2$ cannot both simultaneously be hydrogen.

The compounds of the present invention inhibit the activity of serine proteases, specifically human leukocyte elastase, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

Preferred compounds of Formula I above are those wherein $R^1$ is hydrogen, lower-alkyl, or lower-alkoxy; $R^2$ is hydrogen or from one to two, the same or different, substituents in any of the 5-, 6-, or 7- positions selected from lower-alkoxy, hydroxy, methylenedioxy, cycloalkyloxy, lower-alkoxypoly-lower-alkyleneoxy, hydroxylower-alkoxy, polyhydroxylower-alkoxy, or acetal or ketal thereof, poly(lower-alkoxy) lower-alkoxy, OCOR, —O—($C_1$–$C_{10}$-alkylene)COOR, or —O—($C_2$–$C_{10}$-alkylene)—N=B; and R and N=B are as defined hereinabove.

Particularly preferred compounds of Formula I above are those wherein $R^1$ is hydrogen, lower-alkyl, or lower-alkoxy; and $R^2$ is hydrogen or from one to two, the same or different, substituents in any of the 5- or 6- positions selected from lower-alkoxy or hydroxy.

The invention further relates to a pharmaceutical composition for the treatment of degenerative diseases which comprises a pharmaceutically acceptable carrier, adjuvant, diluent or vehicle together with an effective proteolytic enzyme inhibiting amount of a compound of the formula:

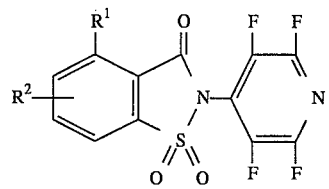

wherein:

$R^1$ is hydrogen, halogen, lower-alkyl, perfluorolower-alkyl, perchlorolower-alkyl, lower-alkenyl, lower-alkynyl, cyano, amino, lower-alkylamino, dilower-alkylamino, lower-alkoxy, benzyloxy, lower-alkoxycarbonyl or phenyl; and $R^2$ is hydrogen or from one to two, the same or different, substituents in any of the 5-, 6- or 7-positions selected from halogen, cyano, nitro, N=B, (where N=B is amino, lower-alkylamino, dilower-alkylamino, 1-azetidinyl, 1-pyrrolidinyl, 1-piperidinyl, 4-morpholinyl, 1-piperazinyl, 4-lower-alkyl-1-piperazinyl, 4-benzyl-1-piperazinyl, 1-imidazolyl, carboxy-lower-alkylamino, or —NR'—($C_1$–$C_{10}$-alkylene)-N(alkyl)$_2$, where R' is lower alkyl), 1-lower-alkyl-2-pyrrolyl, lower-alkylsulfonylamino, polyfluorolower-alkyl-sulfonylamino, polychlorolower-alkylsulfonylamino, aminosulfonyl, lower-alkyl, polyfluorolower-alkyl, polychlorolower-alkyl, cycloalkyl, lower-alkoxy, hydroxy, carboxy, carboxamido, hydroxylower-alkyl, methylenedioxy, cycloalkyloxy, formyl, aminomethyl, lower-alkylsulfonyl, polyfluorolower-alkylsulfonyl, polychlorolower-alkylsulfonyl, lower-alkylsulfonylaminosulfonyl, di(lower-alkyl) phosphonoxy, lower-alkoxypoly-lower-alkyleneoxy, hydroxy-lower-alkoxy, polyhydroxylower-alkoxy, or acetal or ketal thereof, poly(lower-alkoxy) lower-alkoxy, —SR, —SOR, —SO$_2$R, —OCOR, —O—($C_1$–$C_{10}$-alkylene)—COOR, —O—($C_1$–$C_{10}$-alkylene)—COOH, —O—($C_2$–$C_{10}$-alkylene)—N= B, where R is lower-alkyl, phenyl, benzyl or naphthyl, or phenyl or naphthyl substituted by from one to two substituents selected from lower-alkyl, lower-alkoxy or halogen and —N=B has the meanings given above;

or acid-addition salts of basic members thereof or base-addition salts of acidic members thereof.

The invention further relates to a method for the treatment of degenerative diseases which comprises administering to a patient in need of such treatment an effective proteolytic enzyme inhibiting amount of a compound of the formula:

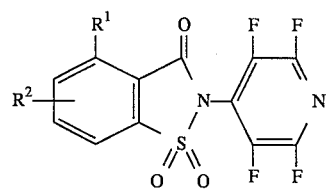

wherein:

$R^1$ is hydrogen, halogen, lower-alkyl, perfluorolower-alkyl, perchlorolower-alkyl, lower-alkenyl, lower-alkynyl, cyano, amino, lower-alkylamino, dilower-alkylamino, lower-alkoxy, benzyloxy, lower-alkoxycarbonyl or phenyl; and $R^2$ is hydrogen or from one to two, the same or different, substituents in any of the 5-, 6- or 7-positions selected from halogen, cyano, nitro, N=B, (where N=B is amino, lower-alkylamino, dilower-alkylamino, 1-azetidinyl, 1-pyrrolidinyl, 1-piperidinyl, 4-morpholinyl, 1-piperazinyl, 4-lower-alkyl-1-piperazinyl, 4-benzyl-1-piperazinyl, 1-imidazolyl, carboxy-lower-alkylamino, or —NR'—($C_1$–$C_{10}$-alkylene)-N(alkyl)$_2$, where R' is lower alkyl), 1-lower-alkyl-2-pyrrolyl, lower-alkylsulfonylamino, polyfluorolower-alkyl-sulfonylamino, polychlorolower-alkylsulfonylamino, aminosulfonyl, lower-alkyl, polyfluorolower-alkyl, polychlorolower-alkyl, cycloalkyl, lower-alkoxy, hydroxy, carboxy, carboxamido, hydroxylower-alkyl, methylenedioxy, cycloalkyloxy, formyl, aminomethyl, lower-alkylsulfonyl, polyfluorolower-alkylsulfonyl, polychlorolower-alkylsulfonyl, lower-alkylsulfonylaminosulfonyl, di(lower-alkyl) phosphonoxy, lower-alkoxypoly-lower-alkyleneoxy, hydroxy-lower-alkoxy, polyhydroxylower-alkoxy, or acetal or ketal thereof, poly(lower-alkoxy) lower-alkoxy, —SR, —SOR, —SO$_2$R, —OCOR, —O—($C_1$–$C_{10}$-alkylene)—COOR, —O— ($C_1$–$C_{10}$-alkylene)—COOH, —O—($C_2$–$C_{10}$-alkylene)-N=B, where R is lower-alkyl, phenyl, benzyl or naphthyl, or phenyl or naphthyl substituted by from one to two substituents selected from lower-alkyl, lower-alkoxy or halogen and —N=B has the meanings given above;

or acid-addition salts of basic members thereof or base-addition salts of acidic members thereof.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, sec-butyl, and the like.

The term lower-alkoxy as used herein means linear or branched alkyloxy substituents having one to about five carbon atoms and thus includes methoxy, ethoxy, propoxy, isopropoxy, butoxy, sec-butoxy, pentoxy, and the like.

The term halogen as used herein means bromine, chlorine, iodine, or fluorine.

The term lower-alkenyl as used herein means linear or branched unsaturated hydrocarbon radicals having two to about four carbon atoms and thus includes ethenyl, 1-propenyl, 2-propenyl, isopropenyl, 1-methyl-2-propenyl, 2-butenyl, isobutenyl, and the like.

The term lower-alkynyl as used herein means linear or branched unsaturated hydrocarbon radicals having two to about four carbon atoms and thus includes ethynyl, 1-propynyl, 2-propynyl, 1-methyl-2-propynyl, 2-butynyl, and the like.

The term hydroxylower-alkyl as used herein means lower-alkyl as defined above substituted by hydroxy and thus includes hydroxymethyl, 1-hydroxy-1-methylethyl, 2-hydroxyethyl, 2-hydroxy- 2-methylpropyl, and the like.

The term cycloalkyloxy as used herein means saturated monocyclic hydrocarbon residues having three to about seven carbon atoms and thus includes cyclopropyloxy, cyclobutyloxy, cyclopentyloxy, cyclohexyloxy and cycloheptyloxy.

The term $C_1$–$C_{10}$ alkylene as used herein means divalent, saturated radicals, including branched chain radicals, of from one to ten carbon atoms and having their free valences on the same or different carbon atoms and thus includes methylene, 1,2-ethylene, ethylidene, 1,3-propylene, propylidene and the like.

The term lower-alkoxy-poly-lower-alkyleneoxy as used herein means such radicals in which lower-alkoxy has the meanings given above, poly means 2 to 4, and lower-alkylene in lower-alkyleneoxy means divalent saturated radicals, including branched radicals, of from two to five carbon atoms. The term thus includes $CH_3(OCH_2CH_2)_p$—O—, $CH_3CH_2[OCH_2CH(CH_3)]_p$—O—, where p=2–4, and the like.

The term hydroxy-lower-alkoxy as used herein means lower-alkoxy as defined above substituted by an hydroxy group other than on the C-1 carbon atom and thus includes 2-hydroxyethoxy and the like.

The term polyhydroxy-lower-alkoxy as used herein means such a group wherein lower-alkoxy is a monovalent aliphatic radical of from two to five carbon atoms substituted by from two to four hydroxy groups none of which are attached to the same or the C-1 carbon atom and thus includes 2,3-dihydroxypropoxy, 2,3,4,5-tetrahydroxypentoxy and the like.

The term poly(lower-alkoxy)-lower-alkoxy as used herein means monovalent aliphatic alkoxy radicals of from three to five carbon atoms substituted by from two to four methoxy or ethoxy groups none of which are attached to the same or the C-1 carbon atom.

The term $C_2$–$C_{10}$ alkylene as used herein means divalent, saturated radicals, including branched chain radicals, of from two to ten carbon atoms and having their free valences on different carbon atoms and thus includes 1,2-ethylene, 1,3-propylene, 1,4-butylene, 1-methyl-1,2-ethylene, 1,8-octylene and the like.

The term cycloalkyl as used herein means $C_3$ through $C_7$ saturated monocyclic hydrocarbon residues and thus includes cyclopropyl, cyclobutyl, cyclopentyl, cyclohexyl and cycloheptyl.

The synthesis of the compounds of the invention may be outlined as shown in Scheme A:

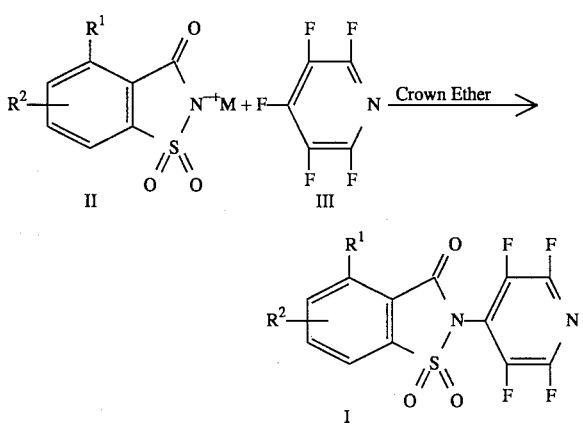

A suitably substituted alkali metal or dilower-alkyl ammonium salt of a 1,2-benzisothiazol-3-(2H)-one 1,1-dioxide of formula II, wherein $M^+$ is an alkali metal, e.g. sodium, or a dilower-alkylamine, e.g. diethylamine, in a suitable solvent, such as acetonitrile, is treated with about one mole or more of pentafluoropyridine (formula III) in the presence of about one mole or more of a suitable crown ether, preferably 15-crown-5, at a temperature in the range of about room temperature up to the boiling point of the solvent used, preferably at the boiling point of the solvent used, to afford the suitably substituted 2-( 2,3,5,6-tetrafluoro-4-pyridyl)-1, 2-benzisothiazole-3(2H)-one 1,1-dioxides of the formula I.

Simple chemical tranformation which are conventional and well known to those skilled in the art of chemistry can be used for effecting changes in the functional groups of the compounds of the Formula I. For example, dealkylation of lower-alkyl phenyl ethers to afford the corresponding phenols and reaction of phenols with alcohols in the presence of a coupling reagent, e.g. a triarylphosphine and a dilower-alkylazodicarboxylate, to produce the corresponding ethers.

The suitably substituted alkali metal salts of the Formula II, wherein $M^+$ is an alkali metal, can be prepared as shown in Scheme B:

Scheme B

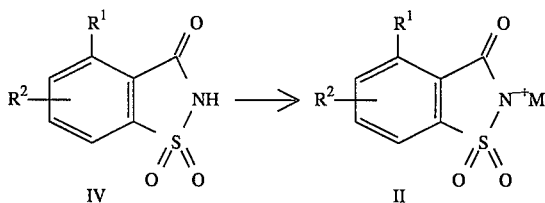

A suitably substituted 1,2-benzisothiazole-3(2H)-one 1,1-dioxide of the formula IV in an appropriate lower-alkanol solvent, e.g. methanol, is treated with approximately one mole or more of an appropriate alkali metal lower-alkoxide, such as sodium methoxide, at a temperature of about room temperature to afford the compounds of the formula II wherein $M^+$ is an alkali metal.

The suitably substituted dilower-alkylammonium salts of the formula II and the suitably substituted 1,2-benzisothiazole- 3-(2H)-one 1,1-dioxides of the formula IV, wherein $R^1$ and $R^2$ are as defined hereinabove, are prepared by the methods described in U.S. Pat. No. 5,128,339, issued Jul. 7, 1992, and allowed U.S. patent application Ser. No. 07/965, 593, which are incorporated herein by reference.

The pentafluoropyridine of the formula III is either commercially available, or it can be prepared by procedures well known in the art.

The compounds of Formula I, which contain basic substituents are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

Likewise, the compounds of Formula I which contain acidic substituents are useful both in the free acid form and in the form of base-addition salts, and, both forms are within the purview of the invention. The base-addition salts are often a more convenient form for use, and in practice, use of the salt form inherently amounts to use of the acid form. The bases which can be used to prepare the base-addition salts include preferably those which produce, when combined with the free acid, pharmaceutically acceptable salts, that is, salts whose cations are relatively innocuous to the animal organism in pharmaceutical doses of the salts, so that the beneficial properties inherent in the free acid are not vitiated by side effects ascribable to the cations. In practicing the present invention it is convenient to use the free acid form or the base-addition salts thereof which are prepared by the reaction of the acid with a base, such as an alkali metal or ammonium hydroxide, or with organic bases such as alkyl, dialkyl or trialkylamines. Although medicinally acceptable salts of the acidic compounds are preferred, all base-addition salts are within the scope of the present invention. All base-addition salts are useful as sources of the free acid form even if the particular salt per se is desired only as an intermediate product, as, for example, when the salt is formed for the purposes of purification or identification, or when it is used as an intermediate in preparing a medicinally acceptable salt.

The structures of the compounds of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points are given in degrees centigrade (°C) and are uncorrected. As used herein, the abbreviation EtOAc stands for ethyl acetate and THF stands for tetrahydrofuran.

EXAMPLE 1

A mixture of the sodium salt of 1,2-benzisothiazol-3(2H)-one 1,1-dioxide (0.81 g, 3.95 mmol), pentafluoropyridine (0.68 g, 4.0 mmol) and 15-Crown-5 (0.88 g, 4.0 mmol) in acetonitrile (15 ml) was heated to reflux for 6 hours, cooled, and the solvent evaporated in vacuo. The oily residue thus obtained was suspended in water and stirred for 3–4 hours. The solid which percipitated was collected by filtration and dried to afford 1.01 g (77%) of 2-( 2,3,5,6-tetrafluoro-4-pyridyl)-1,2-benzisothiazol-3(2H)-one 1,1-dioxide, m.p. 164°–165° C. after recrystallization from carbon tetrachloride.

EXAMPLE 2

The sodium salt of 4-isopropyl-6-methoxy-1,2-benzisothiazol- 3(2H)-one 1,1-dioxide was prepared from 4-isopropyl- 6-methoxy-1,2-benzisothiazol-3(2H)-one 1,1-dioxide (1.0 g, 3.92 mmol) and sodium methoxide (0.21 g) in methanol. The salt was isolated by removing the solvent under reduced pressure and drying under high vacuum for 1 hour. The dried salt was suspended in acetonitrile and then pentafluoropyridine (0.67 g, 3.96 mmol) and 15-Crown-5 (0.87 g, 3.95 mmol) were added. The mixture was heated to reflux for 6–7 hours, cooled, and the solvent was removed in vacuo. The residue was extracted with dichloromethane (100 ml), washed with water, then brine, and then the organic layer was dried over sodium sulfate. The solvent was removed in vacuo, and the residue was purified by column chromatography on silica gel eluting with 10% ethyl acetate/hexane to afford 1.07 g (68%) of 4-isopropyl- 6-methoxy-2-(2,3,5,6-tetrafluoro-4-pyridyl)-1,2-benzisothiazol- 3(2H)-one 1,1-dioxide, m.p. 107°–109° C.

Following procedures similar to those described in Example 2, but substituting an appropriately substituted 1,2-benzisothiazol- 3(2H)-one 1,1-dioxide for 4-isopropyl-6-methoxy-1,2-benzisothiazol- 3(2H)-one 1,1-dioxide or an appropriately substituted dilower-alkylammonium salt of a 1,2-benzisothiazol- 3(2H)-one 1,1-dioxide for the sodium salt of 4-isopropyl-6-methoxy- 1,2-benzisothiazol-3(2H)-one 1,1-dioxide there was prepared the following compounds of the Formula I illustrated in Table I.

eluting with 40% ethyl acetate/hexane to afford 0.3 g (62%) of 4-isopropyl- 6-hydroxy-2-(2,3,5,6-tetrafluoro-4-pyridyl)-1,2-benzisothiazol-1,2-benzisothiazol- 3(2H)-one 1,1-dioxide, m.p. 164.5°–165.5° C.

EXAMPLE 12

A solution of 4-isopropyl-6-hydroxy-2-(2,3,5,6-tetrafluoro- 4-pyridyl)-1,2-benzisothiazol-3(2H) one 1,1-dioxide (0.5 g, 1.28 mmol) in THF was treated with triphenylphosphine (0.34 g, 1.29 mmol), then isopropanol (0.1 ml, 1.28 mmol) and finally diethylazodicarboxylate (0.2 ml, 1.26 mmol), and was then stirred for 10–15 hours at room temperature. The reaction mixture was purified by column chromatography on silica gel eluting with 20% ethyl acetate/hexane to afford 0.45 g (81%) of 4-isopropyl-6-isopropoxy-2-(2,3,5,6-tetrafluoro-4-pyridyl)-1.2-benzisothiazol- 3(2H)-one 1,1-dioxide, m.p. 129.5°–130.5°C.

Following procedures similar to those described in Example 2, but substituting an appropriately substituted 1,2-benzisothiazol- 3(2H) one 1,1-dioxide, for 4-isopropyl-6-methoxy-1,2-benzisothiazol- 3-(2H)-one 1,1-dioxide, or an appropriately substituted dilower-alkylammonium salt of

TABLE I

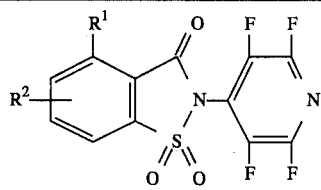

| Example Number | $R^1$ | $R^2$ | M.P. (°C.) | Yield (%) | Chromatography Solvent | |
|---|---|---|---|---|---|---|
| 3 | $CH(CH_3)_2$ | 5,6-$(OCH_3)_2$ | 165.5–166.5 | 81 | 10% EtOAc/hexane | (a) |
| 4 | $OCH_3$ | 6-$OCH_3$ | 234–235.5 | 43 | 40% EtOAc/hexane | (b) |
| 5 | $OCH_3$ | 5-$OCH_3$ | 172.5–173.5 | 53 | 50% EtOAc/hexane | (b) |
| 6 | n-Propyl | 5,6-$(OCH_3)_2$ | 132–134 | 28 | 20% EtOAc/hexane | (a) |
| 7 | $OCH_3$ | H | 204–205 | 87 | 50% EtOAc/hexane | (a, c) |
| 8 | $OC_2H_5$ | H | 182.5–183.5 | 79 | 40% EtOAc/hexane | (d) |
| 9 | $OCH(CH_3)_2$ | H | 153–154 | 82 | 30% EtOAc/hexane | (d) |
| 10 | $CH(CH_3)_2$ | H | 122–124 | 66 | 20% EtOAc/hexane | (a) |
| 10A | H | 6-$OCH_3$ | 169–170 | 97 | | (a) (e) |

(a) Starting material was the sodium salt.
(b) Starting material was the diethylammonium salt.
(c) The reaction mixture was worked-up by removing the solvent, treating the residue thus obtained with water, and collecting the precipitated product by filtration.
(d) The starting material was the sodium salt which was prepared from the corresponding diethylammonium salt which was passed through a ion-exchange resin column (H$^+$ form) to afford the free 1,2-benzisothiazol-3(2H)-one 1,1-dioxide derivative which was then converted into the sodium salt by the procedures described in Example 2.
(e) Recrystallized from ethyl acetate/hexane.

EXAMPLE 11

Ethanethiol (0.82 ml, 11.26 mmol) was added to a suspension of aluminium chloride (0.99 g, 7.42 mmol) in chloroform (20 ml) at 0° C. The mixture was stirred for 10 minutes then a solution of 4-isopropyl-6-methoxy 2-(2,3,5, 6-tetrafluoro-4-pyridyl) 1,2-benzisothiazol-3(2H)-one 1,1-dioxide (0.5 g, 1.73 mmol) in chloroform (10 ml) was added. The mixture was stirred at room temperature for 2–3 hours, then at reflux for 48 hours. The mixture was then cooled, poured over ice-water, acidified with dilute hydrochloric acid and then extracted with ethyl acetate. The organic layer was washed with water, then brine, and then was dried over sodium sulfate. The solvent was removed in vacuo and the residue was purified by column chromatography on silica a 1,2-benzisothiazol-3 (2H)one 1,1-dioxide for the sodium salt of 4-isopropyl-6-methoxy- 1,2-benzisothiazol-3(2H)-one 1,1-dioxide, it is contemplated that there can be prepared the following compounds of the Formula I illustrated in Table II.

TABLE II

| Example Number | R¹ | R² |
|---|---|---|
| 13 | n-butyl | H |
| 14 | Cl | H |
| 15 | Ph | H |
| 16 | H | 7-Cl |
| 17 | —C(O)OCH₃ | H |
| 18 | H | 6-NO₂ |
| 19 | H | 4,7-O(CH₃)₂ |
| 20 | OC₂H₅ | 7-[O(CH₂)₂O(CH₂)₂OCH₃] |
| 21 | CH(CH₃)₂ | 6-N(CH₃)₂ |
| 22 | CH(CH₃)₂ | 6,7-OCH₂O— |
| 23 | CH₃ | 7-CH₃ |
| 24 | CF₃ | H |
| 25 | CCl₃ | H |
| 26 | H | 6-cyclohexyl |
| 27 | H | 6-CH₃O₂NH |
| 28 | H | 6-CF₃SO₂NH |
| 29 | H | 6-CCl₃SO₂NH |
| 30 | H | 6-CN |
| 31 | H | 6-NH₂SO₂ |
| 32 | H | 6-CH₃SO₂NHSO₂ |
| 33 | H | 6-CH₃SO₂ |
| 34 | H | 6-CF₃SO₂ |
| 35 | H | 6-HOOC |
| 36 | H | 6-HOCH₂ |
| 37 | H | 6-OHC |
| 38 | H | 6-NH₂CH₂ |
| 39 | H | 6-CF₃ |
| 40 | H | 6-CCl₃ |
| 41 | CHCH₂ | H |
| 42 | CCH | H |
| 43 | NH₂ | H |
| 44 | CH₃NH | H |
| 45 | (CH₃)₂N | H |
| 46 | CH(CH₃)₂ | 6-CH₃S |
| 47 | CH(CH₃)₂ | 6-CH₃SO |
| 48 | CH(CH₃)₂ | 6-CH₃SO₂ |
| 49 | CH(CH₃)₂ | 6-F |
| 50 | CH(CH₃)₂ | 6-C₆H₅S |
| 51 | CH(CH₃)₂ | 6-(4-CH₃C₆H₄S) |
| 52 | CH(CH₃)₂ | 6-(4-CH₃OC₆H₄S) |
| 53 | CH(CH₃)₂ | 6-(4-ClC₆H₄S) |
| 54 | CH(CH₃)₂ | 6-(4-CH₃-1-naphthyl-S) |
| 55 | CH(CH₃)₂ | 6-(1-naphthyl-S) |
| 56 | CH(CH₃)₂ | 6-C₆H₅SO |
| 57 | CH(CH₃)₂ | 6-C₆H₅SO₂ |
| 58 | CH(CH₃)₂ | 6-(4-CH₃C₆H₄SO) |
| 59 | CH(CH₃)₂ | 6-(4-CH₃C₆H₄SO₂) |
| 60 | CH(CH₃)₂ | 6-(4-CH₃OC₆H₄SO) |
| 61 | CH(CH₃)₂ | 6-(4-CH₃OC₆H₄SO₂) |
| 62 | CH(CH₃)₂ | 6-(4-ClC₆H₄SO) |
| 63 | CH(CH₃)₂ | 6-(4-ClC₆H₄SO₂) |
| 64 | CH(CH₃)₂ | 6-(4-CH₃-1-naphthyl—SO) |
| 65 | CH(CH₃)₂ | 6-(4-CH₃-1-naphthyl—SO₂) |
| 66 | CH(CH₃)₂ | 6-(1-naphthyl—SO) |
| 67 | CH(CH₃)₂ | 6-(1-naphthyl—SO₂) |
| 68 | CH(CH₃)₂ | 6-CH₃COO |
| 69 | CH(CH₃)₂ | 6-C₆H₅COO |
| 70 | CH(CH₃)₂ | 6-(1-naphthyl-COO) |
| 71 | CH(CH₃)₂ | 6-(1-azetidinyl) |
| 72 | CH(CH₃)₂ | 6-(1-pyrrolidinyl) |
| 73 | CH(CH₃)₂ | 6-(1-piperidinyl) |
| 74 | CH(CH₃)₂ | 6-(4-morpholinyl) |
| 75 | CH(CH₃)₂ | 6-(4-benzyl-1-piperazinyl) |
| 76 | CH(CH₃)₂ | 6-(4-methyl-1-piperazinyl) |
| 77 | CH(CH₃)₂ | 6-(1-1H-imidazolyl) |
| 78 | CH(CH₃)₂ | 6-(NHCH₂COOC₄H₉-t) |
| 79 | CH(CH₃)₂ | 6-NH₂ |
| 80 | CH(CH₃)₂ | 6-(1-piperazinyl) |
| 81 | CH(CH₃)₂ | 6-(NHCH₂COOH) |
| 82 | CH(CH₃)₂ | 6-(CH₃CONH) |
| 83 | CONH₂ | H |
| 84 | CN | H |
| 85 | H | CONH₂ |

Following a procedure similar to that described in Example 12, but substituting an appropriate alcohol for isopropyl, it is contemplated that the following compounds illustrated in Table III can be prepared.

TABLE III

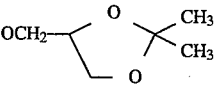

| Example Number | R² |
|---|---|
| 86 | 6-OCH₂—C(CH₃)₂—O (dioxolane structure with CH₃, CH₃) |
| 87 | 6-OCH₂C(O)OCH₃ |
| 88 | 6-OCH₂CH(OCH₃)CH₂OCH₃ |
| 89 | 6-O-cyclobutyl |

Biological Test Results

Representative examples of the compounds of the invention have been found to possess valuable pharmacological properties. In particular, they have been found to inhibit the activity of serine proteases, specifically human leukocyte elastase, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

The pharmacological properties of representative examples of the compounds of the invention were demonstrated by the following conventional in vitro biological test procedure.

The test compound (inhibitor) is dissolved in DMSO in a vial to produce an inhibitor stock solution which has a concentration in the range of 200–1000 μM. The inhibitor stock solution is diluted (1:4, 1:16 and 1:64) into assay vials (vials 1, 2 and 3 respectively) containing 2.4 mL of buffer solution (50 mM N-[2-hydroxyethyl] piperazine-N'-[2-ethanesulfonic acid]/NaOH, 500 mM NaCl, pH 7.8 at 25° C.) and DMSO is added so that the total volume in each vial is 3.2 mL. 70 μL, 50 μL, 35 μL and 25 μL of inhibitor from assay vial 1 is placed into the first four wells of a 96-well microtiter plate and each well is made up to 90 μL total volume with the addition of a 25% DMSO/buffer solution. The inhibitor from assay vials 2 and 3 is processed in a similar manner and placed in wells 5–12 respectively to afford a total of 12 different inhibitor concentrations. Four wells (wells 13–16) containing 90 μL of the 25% DMSO/buffer solution but no inhibitor are also run simultaneously with the inhibited wells as a control. 150 μL of substrate solution (prepared by the addition of 500 μL of the human leukocyte elastase (HLE) substrate MeOSuc-Ala-Ala-Pro-Val-pNA (18.7 mM in DMSO) to 19.5 mL of buffer solution) was then added simultaneously into each of the 16 wells and the solution in each well was thoroughly mixed.

The 96-well microtiter plate was placed into a Microplate Reader #89815A spectrophotometer 110 μL of the enzyme solution (prepared as follows: a mixture of 20 mL of buffer solution and 20 mg of bovine serum albumen is gently vortexed in a scintillation vial and 5 μL HLE stock solution (1 mg/mL dissolved in deionized water) is added simultaneously to each of the 16 wells. Each of the solutions in the wells is throughly mixed and then the time-dependent absorbance data is collected at an absorbance of 410 nM until the assay is complete. It should be noted that although this assay method can be done manually, it is preferred to perform the assay robotically using a Hewlett Packard MicroAssay System Robot.

A plot of the absorbance versus time data thus obtained affords progress curves the final slope of which is equal to the final steady-state velocities (VF). Using the program. ENZFITTER (Elsevier software), the progress curves for the four control assays ([I]=0) are fit by linear regression to yield the enzyme reaction velocity values in the absences of inhibitor ($V_o$) which are averaged to produce a single fixed value. The inhibition constant $K_i$ (nM) is then obtained from a plot of $$\frac{[I]}{1 - V_F/V_o} \text{ versus } V_o/V_F$$

which affords a linear plot wherein:

$$\text{slope} = K_i \left( 1 + \frac{[S]}{Km} \right)$$

and [S] is the concentration of the substrate and $K_m$ is the Michaelis constant.

Table IV summarizes the results obtained from the testing of representative compounds of the invention for human leukocyte elastase inhibitory activity.

TARLE IV

| Example Number | $K_i$ (nM) |
| --- | --- |
| 1 | 20 |
| 2 | 38 |
| 3 | 47.5 |
| 4 | 4 |
| 5 | 15 |
| 6 | 16 |
| 7 | 6.5 |
| 8 | 1.4 |
| 9 | 140 |
| 10 | 100 |
| 10A | 74 |

TARLE IV-continued

| Example Number | $K_i$ (nM) |
| --- | --- |
| 11 | 2000 |
| 12 | 50 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

I claim:

1. A compound of the formula:

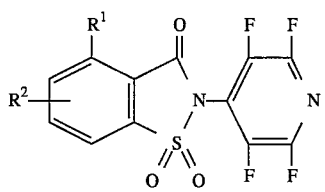

wherein:

R¹ is hydrogen, $C_{3-4}$ alkyl, or C1–4 alkoxy; and

R² is hydrogen or from one to two, the same or different, substituents in any of the 5-, 6- or 7-positions selected from halogen, C1–4 alkoxy, or hydroxy;

or an acid-addition salt of basic members thereof or a base-addition salt of acidic members thereof, with the proviso that R¹ and R² cannot both simultaneously be hydrogen.

2. A compound according to claim 1 wherein R¹ is hydrogen, isopropyl, propyl, methoxy, ethoxy, or isopropoxy; and R² is hydrogen, methoxy, isopropoxy, or hydroxy.

3. A compound selected from 4,6-dimethoxy- 2-(2,3,5,6-tetrafluoro-4-pyridyl)-1,2-benzisothiazol- 3(2H)-one 1,1-dioxide and 4-ethoxy-2-(2,3,5,6-tetrafluoro-4-pyridyl)- 1,2-benzisothiazol-3-(2H)-one 1,1-dioxide or an acid-addition salt of basic members thereof or a base-addition salt of acidic members thereof.

4. A pharmaceutical composition for the treatment of degenerative diseases which comprises a pharmaceutically acceptable carrier, adjuvant, diluent or vehicle together with an effective proteolytic enzyme inhibiting amount of a compound of the formula:

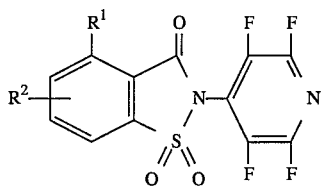

wherein:

R¹ is hydrogen, $C_{3-4}$ or C1–4 alkoxy; and

R² is hydrogen or from one to two, the same or different, substituents in any of the 5-, 6- or 7-positions selected from halogen, C1–4 alkoxy, or hydroxy;

or an acid-addition salt of basic members thereof or a base-addition salt of acidic members thereof.

5. A pharmaceutical composition according to claim 4 wherein R¹ is hydrogen, isopropyl, propyl, methoxy, ethoxy, or isopropoxy; and R² is hydrogen, methoxy, isopropoxy, or hydroxy.

6. A pharmaceutical composition selected from 4,6-dimethoxy-2-(2,3,5,6-tetrafluoro-4-pyridyl)-1,2-benzisothiazol- 3(2H)-one 1,1-dioxide and 4-ethoxy-2-(2,3,5,6-tetrafluoro- 4-pyridyl)-1,2-benzisothiazol-3-(2H)-one 1,1-dioxide or an acid-addition salt of basic members thereof or a base-addition salt of acidic members thereof.

* * * * *